United States Patent [19]

Kawa et al.

[11] Patent Number: 4,892,728

[45] Date of Patent: Jan. 9, 1990

[54] PUMPABLE CATIONIC FATTY ALCOHOL DESPERSION

[75] Inventors: Rolf Kawa, Monheim; Holger Tesmann, Duesseldorf; Josef Wilhelm; Karl-Heinz Rose, both of Huenfeld; Eugen Konrad, Darmstadt, all of Fed. Rep. of Germany

[73] Assignee: Henkel Kommanditgesellschaft auf Aktien, Duesseldorf, Fed. Rep. of Germany

[21] Appl. No.: 168,844

[22] Filed: Mar. 16, 1988

[30] Foreign Application Priority Data

Mar. 16, 1987 [DE] Fed. Rep. of Germany ....... 3708425

[51] Int. Cl.$^4$ .................. A61K 7/075; A61K 7/08; A61K 7/021; B01F 17/18
[52] U.S. Cl. ..................... 424/70; 514/772; 514/788; 514/937; 424/63; 252/357
[58] Field of Search ................ 252/312, 357; 424/63, 424/70; 514/772, 788, 937, 938

[56] References Cited

U.S. PATENT DOCUMENTS 4,213,867  7/1980  Cukier et al. ............... 252/8.75

FOREIGN PATENT DOCUMENTS 3440935  11/1984  Fed. Rep. of Germany .
3417646  11/1985  Fed. Rep. of Germany ........ 424/70
8803016   5/1988  PCT Int'l Appl. .

OTHER PUBLICATIONS

G. T. Baley, G. E. Peck, & G. S. Banker, *Journal of Pharmaceutical Sciences*, vol. 66, No. 5, pp. 696–699 (May 1977).

Primary Examiner—Ellis P. Robinson
Assistant Examiner—Susan S. Rucker
Attorney, Agent, or Firm—Ernest G. Szoke; Wayne C. Jaeschke; Daniel S. Ortiz

[57] ABSTRACT

The present invention relates to a pumpable cationic fatty alcohol dispersion having a high content of dispersed fatty alcohol and a low content of cationic dispersant, characterized in that it contains:

(A) from more than 10 to about 25.0% by weight of a linear or branched, primary, saturated $C_{14}$–$C_{22}$ fatty alcohol;

(B) from about 0.01 to about 1% by weight of a cationic surface-active compound containing a quaternary ammonium, pyridinium or imidazolinium group and a linear $C_8$–$C_{22}$ alkyl or 2-hydroxyalkyl group; and (C) water quantity sufficient to adjust to 100% by weight.

It has surprisingly been found that the fatty alcohol dispersions according to the invention can be stabilized with very small quantities of the cationic surface-active compound and that, despite high fatty alcohol contents, a low viscosity and hence good pumpability of the dispersion can be obtained, particularly with low contents of cationic dispersant.

20 Claims, No Drawings

PUMPABLE CATIONIC FATTY ALCOHOL DESPERSION

BACKGROUND OF THE INVENTION

1. Field of the Invention

This invention relates to a pumpable cationic fatty alcohol dispersion having a high content of dispersed fatty alcohol and a low content of cationic dispersant.

2. Statement of Related Art

The production of numerous liquid, aqueous and emulsion-form skin-care and hair-care preparations involves the use of fatty alcohols which, in dispersed form in these preparations, provide the skin with a smooth and supple surface and the hair with improved combability and softness. The incorporation of the fatty alcohols, which are solid wax-like substances at normal temperature, requires melting and uniform, stable dispersion in the similarly heated solution or emulsion of the other components. This procedure involves considerable technical outlay, and therefore it would be of considerable advantage for many manufacturers of cosmetics if the fatty alcohol were available in the form of a stable dispersion concentrate which could be added to the preparations without heating and without any need to use special dispersion units, and could be uniformly dispersed therein simply by stirring.

It would be particularly advantageous to prepare aqueous fatty alcohol dispersions at as high a concentration of fatty alcohol content as possible while at the same time maintaining the stability of the dispersion and maintaining a viscosity which will permit the dispersion to be pumpable at ambient temperatures, i.e., at Brookfield viscosities of 0.5 to 10 Pascals as measured with a #5 spindle at 20° C.

It is known in the art that cationic surface-active compositions may be used to stabilize aqueous dispersions containing fatty alcohols. For example, German patent document DE 3440935 discloses aqueous hair care preparation compositions containing a mixture of coconut fatty acid mono-ethanolamide, from 0.4 to 10% by weight of at least one linear $C_{14}$ to $C_{18}$ fatty alcohol and 0.1 to 1.5% by weight of a quaternary ammonium and/or pyridinium organic compound. Similar quaternary ammonium compounds, particularly lauryl, myristyl, cetyl and stearyl trimethylammonium bromides, are known to have anti-bacterial properties when used in cosmetic preparations also containing fatty alcohol dispersions, such as disclosed by G. T. Baley, G. E. Peck and G. S. Banker, J. Pharm Sci, 68, pp 696–600 (1977).

It would normally be expected that as the amount of the fatty alcohol content of aqueous dispersions is increased and the viscosity increases, a concomitant increase in the content of cationic surface-active ingredient, e.g., the quaternary compound, would be required to maintain the dispersion in a readily flowable and pumpable state.

It has been surprisingly discovered in accordance with the present invention that stable aqueous concentrates having high fatty alcohol contents of greater than 10% by weight, for example 15–25% by weight, are rendered more pumpable and have lower viscosities where the amount of cationic surface-active agent is reduced rather than increased.

SUMMARY OF THE INVENTION

The present invention relates to a pumpable cationic fatty alcohol dispersion having a high content of dispersed fatty alcohol and a low content of cationic dispersant, characterized in that it contains:

(A) from more than 10 to 25.0% by weight of a linear or branched, primary, saturated $C_{14}$–$C_{22}$ fatty alcohol;

(B) from 0.01 to 1% by weight of a cationic surface-active compound containing a quaternary ammonium, pyridinium or imidazolinium group and a linear $C_8$–$C_{22}$ alkyl or 2-hydroxyalkyl group; and (C) water in a quantity sufficient to adjust to 100% by weight.

It has surprisingly been found that the fatty alcohol dispersions according to the invention can be stabilized with very small quantities of the cationic surface-active compound and that, despite high fatty alcohol contents, a low viscosity and hence good pumpability of the dispersion can be obtained, particularly with low contents of cationic dispersant.

DETAILED DESCRIPTION OF THE INVENTION

Other than in the operating examples, or where otherwise indicated, all numbers expressing quantities of ingredients or reaction conditions used herein are to be understood as modified in all instances by the term "about".

In the more preferred embodiment of this invention, the fatty alcohol content of the aqueous dispersions ranges from 15 to 25% by weight, most preferably from 20 to 25% by weight; the content of cationic surface-active compound ranges from 0.01 to 0.5%, more preferably from 0.01 to 0.3% by weight, and most preferably from 0.01 to 0.2% by weight.

In general, the fatty alcohol compositions are formulated to contain 70.0 to 89.0% by weight water, more preferably 74.0 to 83.0 by weight water.

Suitable fatty alcohols for the purpose of the invention include myristyl alcohol, cetyl alcohol, stearyl alcohol, arachidyl alcohol or behenyl alcohol. The fatty alcohols may be present either individually or in the form of technical mixtures. Cetyl and/or stearyl alcohol are particularly suitable. These alcohols are also commercially available as cetostearyl alcohol cuts with different contents of cetyl alcohol and stearyl alcohol.

Suitable cationic, surface-active compounds having a dispersing effect necessary for the purposes of the invention are compounds which, in addition to a water-solubilizing quaternary ammonium, pyridinium or imidazolinium group, contain a lipophilic, linear $C_8$–$C_{22}$ alkyl or 2-hydroxyalkyl group. Compounds such as these include, for example, cetyl pyridinium chloride, 2-alkyl($C_{15}$)-1-(2'-hydroxyethyl)-1-methyl imidazolinium methosulfate, 2-undecyl-1-(2-hydroxyethyl)-1-methyl imidazolinium chloride and 2-tallow alkyl-1-tallow acyl aminoethyl ethyl imidazoliniumethosulfate.

Among the numerous quaternary ammonium compounds, compounds corresponding to the following formula are particularly important for the purposes of this invention:

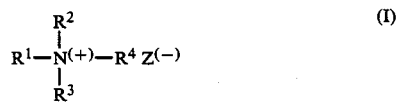

wherein $R^1$ is selected from the group consisting of a $C_8$–$C_{22}$ alkyl or 2-hydroxyalkyl group, and a group of the formula $R^5CONH(CH_2)_x$—, where $R^5$ is a $C_7$–$C_{21}$ alkyl group and x is a number of from 2 to 4; $R^2$ and $R^3$ are selected from the group consisting of a $C_1$–$C_4$ alkyl group and a group of the formula —$(C_nH_{2n}O)_y$—H, where n is an integer of from 2 to 4 and y is a number of from 1 to 10; $R^4$ is a benzyl group or has one of the meanings defined for $R^2$ and $R^3$; and $Z^{(-)}$ is an anion selected from the group consisting of chloride, bromide, hydrogen sulfate, hydrogen phosphate, methoxysulfate and ethoxysulfate.

Such cationic surface-active compounds have particularly good dispersing effect. Examples of preferred compounds include cetyl trimethyl ammonium chloride, lauryl dimethyl benzyl ammonium chloride, 2-hydroxycetyl-2-hydroxyethyl dimethyl ammonium chloride, lauryl trimethyl ammonium chloride or behenyl trimethyl ammonium chloride. Cationic surfactants of this type are known and are available commercially. For example, Adogen TM 444 is trademark of Sherex Chemical Co., USA, for trimethyl cetyl quaternary ammonium chloride and is disclosed to be useful for an "emulsifier, dispersant, creme-rinse, fermentation aid" in McCutcheon's Emulsifiers and Detergents, 1984, North American Edition, M. C. Publishing Co., Glen Rock, N.J. at page 71.

Among the cationic surface-active quaternary ammonium compounds corresponding to formula (I), those in which $R^1$ is a $C_{12}$–$C_{18}$ alkyl or 2-hydroxyalkyl group, $R^2$, $R^3$ and $R^4$ are methyl or 2-hydroxyethyl groups and $Z^{(-)}$ is a chloride anion are particularly preferred as dispersants for the fatty alcohol dispersion according to the invention.

In addition, the fatty alcohol dispersions according to the invention may contain other auxiliaries and additives in small quantities of up to about 5% by weight, including for example paraffins, glycerol monostearate, ethylene glycol distearate, fatty acid alkanolamides, perfumes, dyes, preservatives, complexing agents or salts and buffer substances.

The pH-value of the fatty alcohol dispersion according to the invention is preferably in the range from pH 2 to pH 10. It may be adjusted by buffer substances suitable for this purpose, such as citric acid or triethanolamine, in a quantity of from 0.1 to 1% by weight.

The fatty alcohol dispersions according to the invention may readily be prepared by heating the fatty alcohol (A) to a temperature above its melting point and mixing and homogenizing the resulting melt in a static or dynamic mixer or dispersion unit at a temperature not greater than about 50° C. above the melting point of the alcohol with a solution of the cationic surface-active compound (B) in water (C) similarly heated beyond the melting point of the fatty alcohol. One particularly effective procedure is characterized in that the fatty alcohol (A) and aqueous solution of the cationic surface-active compound (B) are heated to 70° to 80° C., combined in a rotor-stator homogenizer, and the dispersion formed is cooled with continuous agitation, for example with stirring, to a temperature below the melting point of the fatty alcohol.

The fatty alcohol dispersion according to the invention has a fluid consistency and, accordingly, is readily pumpable even at normal temperature (20° C.). Its viscosity is generally in the range from 0.5 to 10 Pa.s (as measured with a Brookfield rotational viscosimeter, spindle No. 5, at 20° C.). In some instances, the viscosity may increase to approximately 50 Pa.s (20°) as a consequence of prolonged storage and with high concentrations of more than 20% by weight of fatty alcohol and more than 0.2% by weight of the cationic surface-active compound. However, the fatty alcohol dispersion according to the invention always retains its good pumpability and can be readily and spontaneously diluted with water or spontaneously dispersed in aqueous preparations. Accordingly, the fatty alcohol dispersion according to the invention represents a particularly favorable and readily processible supply form for fatty alcohols.

The dispersions are particularly suitable for the production of aqueous cosmetic hair-care and skin-care preparations containing $C_{14}$–$C_{22}$ fatty alcohols in finely dispersed form. The fatty alcohol dispersions according to the invention are used particularly preferably for the production of hair aftertreatment preparations or hair rinses which are applied to the hair after shampooing to improve combability, to reduce static chargeability and to provide the hair with shine, hold and body. For this purpose, typical hair rinses contain from 0.5 to 5% by weight fatty alcohol in finely dispersed form according to this invention and from 0.3 to 3% by weight of further cationic surface-active compounds. Hair rinses such as these may be prepared from the fatty alcohol dispersion according to the invention at normal temperatures by corresponding dilution with an aqueous solution of a cationic surface-active compound without any need to use special homogenizers or dispersion units.

The following Examples are intended to illustrate the invention without limiting it in any way.

EXAMPLES 1-15

Fifteen different fatty alcohol dispersions having the composition shown in Tables I and II were prepared as follows:

A mixture of water and quaternary ammonium compound was heated to 75° C. and dispersed with a melt of the fatty alcohols heated to 75° C. in a homogenizer of the rotor-stator type using intense shear forces. The dispersion was then cooled to 40° C. with continuous stirring.

The fatty alcohol dispersions described in Tables I and II remained unchanged, i.e. stable, for 4 weeks. In general, they underwent a slight increase in viscosity in the first week.

TABLE I

|  | 1* | 2 | 3 | 4 | 5 | 6 | 7 | 8 | 9 |
|---|---|---|---|---|---|---|---|---|---|
| Cetyl/stearyl alcohol (1:1 molar ratio) | 15 | 15 | 15 | 20 | 20 | 20 | 25 | 25 | 25 |
| Cetyl trimethyl ammonium chloride | 0.025 | 0.05 | 0.1 | 0.025 | 0.05 | 0.1 | 0.025 | 0.1 | 0.2 |
| Water | **ad 100 | ad 100 | ad 100 | ad 100 | ad 100 | ad 100 | ad 100 | ad 100 | ad 100 |
| Viscosity, Brookfield RVF rotational viscosimeter, spindle no. 5, 10 r.p.m., 20° C. |  |  |  |  |  |  |  |  |  |
| After 24 hours (Pa.s)*** | 1.6 | 3.8 | 7.2 | 1.8 | 4.0 | 9.2 | 4.8 | 11.6 | 19.2 |

TABLE I-continued

|  | 1* | 2 | 3 | 4 | 5 | 6 | 7 | 8 | 9 |
|---|---|---|---|---|---|---|---|---|---|
| After 7 days (Pa.s) | 2.4 | 4.4 | 9.2 | 2.4 | 5.0 | 11.2 | 4.8 | 13.2 | 28.0 |

*Quantities are percent by weight.
**Water to bring to 100%.
***1 Pascal second (Pa.s) approximates 1 centipoise second (cps)

TABLE II

|  | 10 | 11 | 12 | 13 | 14 | 15 |
|---|---|---|---|---|---|---|
| Myristyl alcohol | 20 | 20 | 20 | — | — | — |
| Behenyl alcohol | — | — | — | 20 | 20 | 20 |
| Cetyl trimethyl ammonium chloride | 0.1 | — | — | 0.1 | — | — |
| 2-Hydroxyethyl-2-hydroxyethyl dimethyl ammonium chloride | — | 0.1 | — | — | 0.1 | — |
| Behenyl trimethyl ammonium chloride | — | — | 0.1 | — | — | 0.1 |
| Water | ad 100 | ad 100 | ad 100 | ad 100 | ad 100 | ad 100 |
| Viscosity, Brookfield RVF rotational viscosimeter, spindle no. 5, 10 r.p.m., 20° C. | | | | | | |
| After 24 hours (Pa.s) | 3 | 4.4 | 8.2 | 14.4 | 11.2 | 4.8 |
| After 7 days (Pa.s) | 11 | 6.5 | 15.2 | 12.4 | 12.8 | 6.8 |

The data in Table 1 demonstrates that the viscosity of the fatty alcohol dispersions actually decreases as a function of decreasing content of the quaternary ammonium compound as can be seen by comparing examples 1–3, or 4–6, or 7–9.

It is to be understood that the above described embodiments of the invention are illustrative only and that modifications throughout may occur to those skilled in the art.

We claim:

1. A cationic fatty alcohol dispersion having a high fatty alcohol content and a viscosity of about 0.5 to about 50 Pa.s at 20° C. comprising a mixture of:
(A) from more than 10 to about 25.0% by weight of a linear or branched, primary, saturated $C_{14}$–$C_{22}$ fatty alcohol or mixtures of such alcohols;
(B) from about 0.01 to about 1.0% by weight of a cationic surface-active compound containing a quaternary ammonium, pyridinium or imidazolinium group and a linear $C_8$–$C_{22}$ alkyl or 2-hydroxyalkyl group; and
(C) water in a quantity sufficient to adjust to 100% by weight.

2. The fatty alcohol dispersion of claim 1 containing:
(A) from about 15.0 to about 25.0% by weight of the fatty alcohol;
(B) from about 0.01 to about 0.5% by weight of the cationic surface-active compound; and
(C) water in a quantity sufficient to adjust to 100% by weight.

3. The fatty alcohol dispersion of claim 2 wherein the cationic surface-active compound is present at a level of about 0.01 to about 0.2% by weight.

4. The fatty alcohol dispersion of claim 3 wherein the fatty alcohol is present at a level of from about 20 to about 25% by weight.

5. The fatty alcohol dispersion of claim 1 wherein the fatty alcohol component (A) is cetyl alcohol, stearyl alcohol or a mixture thereof.

6. The fatty alcohol dispersion of claim 1 wherein the cationic surface-active compound (B) is a quaternary ammonium compound having the following formula:

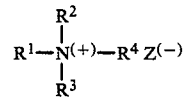

wherein $R^1$ is selected from the group consisting of a $C_8$–$C_{22}$ alkyl or 2-hydroxyalkyl group, and a group of the formula $R^5CONH(CH_2)_x$—, where $R^5$ is a $C_7$–$C_{21}$ alkyl group and x is a number of from 2 to 4; $R^2$ and $R^3$ are selected from the group consisting of a $C_1$–$C_4$ alkyl group and a group of the formula —$(C_nH_{2n}O)_y$—H, where n is an integer of from 2 to 4 and y is a number of from 1 to 10; $R^4$ is a benzyl group or has one of the meanings defined for $R^2$ and $R^3$; and $Z^{(-)}$ is an anion selected from the group consisting of chloride, bromide, hydrogen sulfate, hydrogen phosphate, methoxysulfate and ethoxysulfate.

7. The fatty alcohol dispersion of claim 6 which additionally contains from about 0.1 to about 1% by weight of buffer substances to adjust the dispersion to a pH value of from 2 to 10.

8. The fatty alcohol dispersion of claim 1 further containing one or more additives selected from the group consisting of paraffins, glycerolmonostreaate, ethylene glycol distearate, fatty acid alkanolamides, perfumes, dyes, preservatives complexing agents, salts and buffer substances.

9. The fatty alcohol dispersion of claim 6 wherein $R^1$ is a $C_{12}$–$C_{18}$ alkyl or 2-hydroxyalkyl group, $R^2$, $R^3$ and $R^4$ are methyl or 2-hydroxyethyl groups and $Z^{(-)}$ is a chloride anion.

10. The fatty alcohol dispersion of claim 9 wherein surface-active component B is cetyl trimethyl ammonium chloride.

11. The fatty alcohol dispersion of claim 9 wherein surface-active component B is 2-hydroxyethyl-2-hydroxyethyl dimethyl ammonium chloride.

12. The fatty alcohol dispersion of claim 9 wherein surface-active component B is behenyl trimethyl ammonium chloride.

13. The fatty alcohol dispersion of claim 9 wherein the fatty alcohol component A is cetyl alcohol, stearyl alcohol or a mixture thereof.

14. A process for the preparation of the fatty alcohol dispersion of claim 1 comprising:

(A) heating fatty alcohol component A to a temperature above its melting point;

(B) heating a solution of cationic surface-active compound B in water to a temperature above the melting point of said fatty alcohol component;

(C) homogeneously mixing said fatty alcohol and said solution at a temperature not greater than about 50° C. above the melting point of said fatty alcohol component to form a dispersion; and (D) cooling the resultant dispersion.

15. The process of claim 14 wherein the heating temperatures range from about 70° C. to about 80° C.

16. The process of claim 14 wherein the fatty alcohol content of the dispersion is within the range of about 15 to about 25% by weight.

17. The process of claim 16 wherein the content of cationic surface-active compound in the dispersion is within the range of about 0.01 to about 0.5% by weight.

18. The process of claim 17 wherein the content of cationic surface-active compound in the dispersion is within the range of about 0.01 to about 0.2% by weight.

19. The process of claim 18 wherein the cationic surface-active compound is present at a level of about 0.025% by weight.

20. The process of any one of claims 16, 17, 18 and 19 wherein the fatty alcohol content of the dispersion is within the range of about 20 to about 25% by weight.

* * * * *